United States Patent [19]

Suresh et al.

[11] 4,317,747

[45] Mar. 2, 1982

[54] PROMOTED U-SB-OXIDE CATALYSTS

[75] Inventors: Dev D. Suresh, Macedonia; Robert K. Grasselli, Chagrin Falls, both of Ohio

[73] Assignee: The Standard Oil Co., Cleveland, Ohio

[21] Appl. No.: 95,886

[22] Filed: Nov. 16, 1979

[51] Int. Cl.$^3$ .......................... B01J 23/12; B01J 23/18; B01J 23/20; B01J 23/24
[52] U.S. Cl. ................................ 252/469; 260/465.3; 562/547; 568/477; 585/626
[58] Field of Search .................... 252/469; 260/465.3; 562/547; 585/626; 568/477

[56] References Cited

U.S. PATENT DOCUMENTS

| | | | |
|---|---|---|---|
| 3,431,292 | 3/1969 | Callahan et al. | 260/465.3 |
| 3,960,925 | 6/1976 | Gasson et al. | 260/465.3 |
| 4,008,179 | 2/1977 | Gasson et al. | 252/469 X |
| 4,018,712 | 4/1977 | Li | 252/456 |
| 4,222,899 | 9/1980 | Innes et al. | 260/465.3 |

*Primary Examiner*—W. J. Shine
*Attorney, Agent, or Firm*—John E. Miller, Jr.; Herbert D. Knudsen; Larry W. Evans

[57] ABSTRACT

Certain multiply promoted U-Sb-oxides are superior catalysts for the ammoxidation of olefins to the corresponding unsaturated nitriles, the selective oxidation of olefins to unsaturated aldehydes and acids, and the oxyde-hydrogenation of olefins to diolefins.

15 Claims, No Drawings

4,317,747

PROMOTED U-SB-OXIDE CATALYSTS

BACKGROUND OF THE INVENTION

The present invention relates to novel uranium antimonate catalysts for use in various oxidation-type reactions, such as the oxidation of olefins to produce aldehydes and acids, the ammoxidation of olefins to produce unsaturated nitriles and the oxydehydrogenation of olefins to diolefins.

U.S. Pat. No. 3,431,292 to Callahan, et al., the disclosure of which is incorporated herein by reference, describes certain promoted uranium antimonate catalysts which are useful in various oxidation-type reactions. Although these catalysts give good yields of the desired end products in various oxidation-type reactions, it is always beneficial to provide new catalysts having superior catalytic properties.

Accordingly, it is an object of the present invention to provide new catalysts capable of providing superior yields of desired end products in various types of oxidation reactions.

SUMMARY OF THE INVENTION

These and other objects are accomplished by the present invention which is based on the discovery that certain uranium antimonate catalysts when promoted with certain combinations of at least three different elements provide excellent yields of desired end products such as, for example, acrylonitrile in various types of oxidation reactions.

Accordingly, the present invention provides new catalysts for use in various types of oxidation reactions, said catalysts comprising a uranium antimonate oxide complex catalyst of the formula:

$$A_aB_bE_cU_dSb_eO_x$$

wherein
A is at least one element selected from Group IB and Group VB of the Periodic Table (Sargent-Welsh);
B is at least one element selected from Group VIB;
E is at least one element selected from Group IVA and Group VIB and thorium; and
wherein
a is 0.001 to 10;
b is 0.001 to 10;
c is 0.001 to 10;
d is 0.1 to 10;
e is 1 to 20;
x is determined by the valence requirements of the other elements present.

In addition, the present invention provides improvements in the known processes for the oxidation of olefins to produce aldehydes and acids, the known processes for the ammoxidation of olefins to produce unsaturated nitriles, and the oxydehydrogenation of olefins to produce diolefins, the improvement in accordance with the invention comprising using as the oxidation catalyst a uranium anti-monate oxide complex defined by the formula:

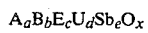

$$A_aB_bE_cU_dSb_eO_x$$

wherein
A is at least one element selected from Group IB and Group VB of the Periodic Table (Sargent-Welsh);
B is at least one element selected from Group VIB;
E is at least one element selected from Group IVA and Group IVB and thorium; and
wherein
a is 0.001 to 10;
b is 0.001 to 10;
c is 0.001 to 10;
d is 0.1 to 10;
e is 1 to 20;
x is determined by the valence requirements of the other elements present.

DETAILED DESCRIPTION

The novel catalyst of the present invention finds significant use in the ammoxidation of olefins to nitriles. They can also be used, however, in the ammoxidation of alcohols and aldehydes to nitriles as well as in the oxidation of olefins to oxygenated compounds and the oxidative dehydrogenation of olefins to diolefins and aromatics.

Ammoxidation

A wide variety of different reactants can be ammoxidized in accordance with the present invention to produce nitriles. For example, olefins such as propylene and isobutylene, alcohols such as t-butyl alcohol, and aldehydes such as acrolein and methacrolein can be readily converted to nitriles in accordance with the present invention. In general, compounds which can be converted to nitriles by the inventive ammoxidation reaction include 3 to 9 carbon atom hydrocarbons unsubstituted or substituted with oxygen or hydroxyl. Preferred starting materials are olefins, aldehydes and alcohols containing 3 or 4 carbon atoms.

The general ammoxidation process for converting olefins, alcohols and aldehydes to nitriles is well known. See, for example, U.S. Pat. No. 3,546,138, the disclosure of which is incorporated herein by reference. In general, the ammoxidation reaction is accomplished by contacting the reactant, oxygen and ammonia with a particular catalyst in the vapor phase. The inventive reaction is carried out in the same manner and under the conditions generally set forth in this patent.

In a preferred aspect, the inventive process comprises contacting a mixture comprising propylene or isobutylene, ammonia and oxygen with the promoted catalyst of this invention is an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give similar results. The molar ratio of oxygen to the olefin in the feed to the reaction vessel should be in the range of 0.5:1 to 4:1 and a ratio of about 1:1 to 3:1 is preferred.

Low molecular weight saturated hydrocarbons do not appear to influence the reaction to an appreciable degree, and these materials can be present; consequently, the addition of saturated hydrocarbons in the reaction feed is contemplated within the scope of this invention. Likewise, diluents, such as nitrogen and the oxides of carbon, may be present in the reaction mixture without deleterious effect.

The molar ratio of ammonia to olefin in the feed to the reactor may vary between about 0.05:1 to 5:1. There is no real upper limit for the ammonia/olefin ratio, but there is generally no reason to exceed the 5:1 ratio. At ammonia/olefin ratios appreciably less than the stoichiometric ratio of 1:1, various amounts of oxygenated derivatives of the olefin will be formed.

Significant amounts of unsaturated aldehydes, as well as nitriles, will be obtained at ammonia-olefin ratios substantially below 1:1, i.e., in the range of 0.15:1 to 0.75:1. Above the upper limit of this range, the amount of aldehydes produced rapidly decreases. It is fortuitous that within the ammonia-olefin range stated, maximum utilization of ammonia is obtained and this is highly desirable. It is generally possible to recycle any unreacted olefin and unconverted ammonia.

Water can also be included in the feed although it is not essential. In some instances, e.g. fixed-bed systems, water may improve the selectivity of the reaction and the yield of nitrile. However, reactions not including water in the feed are also within the scope of the present invention.

In general, the molar ratio of added water to olefin, when water is added, is in the neighborhood of 0.1:1 or higher. Ratios on the order of 1:1 to 3:1 are particularly desirable, but higher ratios may be employed, i.e. up to about 10:1.

The reaction is carried out at an elevated temperature such as 200° C. to 600° C., preferably 400° C. to 500° C. The pressure at which the reaction is conducted is also an important variable, and the reaction should be carried out at about atmospheric or slightly above atmospheric (2 to 3 atmospheres) pressure. In general, high pressures, i.e. above 15 atmospheres, are not suitable since higher pressures tend to favor the formation of undesirable byproducts.

The apparent contact time is not critical, and contact times in the range of from 0.1–50 seconds may be employed. The optimal contact time will, of course, vary depending upon the reactant being used, but in general, contact time of from 1–15 seconds is preferred.

The inventive ammoxidation reaction is carried out in the vapor phase. Normally, the process is conducted on a continuous basis using either a fixed-bed or a fluid-bed catalyst. However, a batch operation can be employed.

The reaction product passing out of the reactor is normally in the form of a gas. Conventionally, this gaseous reaction product is treated to remove $NH_3$ and then partially condensed either by indirect contact with a cooling medium or direct contact with water to form a liquid phase containing acrylonitrile, acrolein, acrylic acid, HCN and acetonitrile and a vapor phase containing $CO_2$, CO, $N_2$ and $O_2$. The acrylonitrile is then separated from the liquid phase by a number of different techniques such as, for example, distillation or water extraction/distillation. Additional steps can be employed to separately recover HCN and/or acetonitrile from the gross reaction product.

Oxidation

As previously indicated, the catalysts of this invention can also be employed in the catalytic oxidation of olefins to various different reaction products.

The reactants used in the oxidation to oxygenated compounds are oxygen and an olefin such as propylene, isobutylene and other olefins having up to three contiguous carbon atoms (i.e. three carbon atoms arranged in a straight chain).

The olefins may be in admixture with paraffinic hydrocarbons, such as ethane, propane, butane and pentane; for example, a propylene-propane mixture may constitute the feed. This makes it possible to use ordinary refinery streams without special preparation.

The temperature at which this oxidation is conducted may vary considerably depending upon the catalyst, the particular olefin being oxidized and the correlated conditions of the rate of throughput or contact time and the ratio of olefin to oxygen. In general, when operating at pressures near atmospheric, i.e. 0.1 to 10 atmospheres, temperatures in the range of 150° C. to 600° C. may be advantageously employed. However, the process may be conducted at other pressures, and in the case where superatmospheric pressures, e.g. above 10 atmospheres are employed, somewhat lower temperatures are possible. In the case where this process is employed to convert propylene to acrolein, a temperature range of 200° C. to 500° C. has been found to be optimum at atmospheric pressure.

While pressures other than atmospheric may be employed, it is generally preferred to operate at or near atmospheric pressure, since the reaction proceeds well at such pressures and the use of expensive high pressure equipment is avoided, and formation of undesired byproducts and waste is diminished.

The apparent contact time employed in the process is not critical and it may be selected from a board operable range which may vary from 0.1 to 50 seconds. The apparent contact time may be defined as the length of time in seconds which a unit volume of gas measured under the conditions of reaction is in contact with the apparent unit volume of the catalyst. It may be calculated, for example, from the apparent volume of the catalyst bed, the average temperature and pressure of the reactor, and the flow rates of the several components of the reaction mixture.

The optimum contact time will, of course, vary depending upon the olefin being treated, but in the case of propylene and isobutylene, the preferred contact time is 0.15 to 15 seconds.

A molar ratio of oxygen to olefin between about 0.5:1 to 5:1 generally gives the most satisfactory results. For the conversion of propylene to acrolein, a preferred ratio of oxygen to olefin is from about 1:1 to about 2.5:1. The oxygen used in the process may be derived from any source; however, air is the least expensive source of oxygen and is preferred for that reason.

The addition of water to the reaction mixture in oxidation reactions can have a beneficial influence on the conversion and yields of the desired product especially in fixed-bed reactions. The manner in which water affects the reaction is not fully understood. In any event, it is preferred in fixed-bed operation to include water in the reaction mixture, and in general a ratio of olefin to water in the reaction mixture of from 1:1.25 to 1:10 will give very satisfactory results while a ratio of 1:0.5 to 1:6 has been found the optimum when converting propylene to acrolein.

Inert diluents such as oxygen and carbon dioxide, may be present in the reaction mixture.

Oxydehydrogenation

In accordance with the present invention, the promoted catalyst system of the present invention can also be employed in the catalytic oxidative dehydrogenation of olefins to diolefins and aromatic compounds. In this process, the feed stream in vapor form containing the olefin to be dehydrogenated and oxygen is conducted over the promoted catalyst at a comparatively low temperature to obtain the corresponding diolefin.

By the term "olefin" as used herein is meant open chain as well as cyclic olefins. The olefins dehydrogenated in accordance with this invention have at least four and up to about nine nonquaternary carbon atoms, of which at least four are arranged in series in a straight chain or ring. The olefins preferably are either normal straight chain or tertiary olefins. Both cis and trans isomers, where they exist, can be dehydrogenated.

Among the many olefinic compounds which can be dehydrogenated in this way are butene-1; butene-2; pentene-1; pentene-2; pentenes, hexenes, etc. such as 2-methylpentene-1,3-methylbutene-1,3,4-dimethyl-pentene-1,4-methylpentene-2; heptene-1; octene-1; cyclopentene; cyclohexene, 3-methyl cyclohexene and cycloheptene.

Open chain olefins yield diolefins, and, in general, six-membered ring olefins yield aromatic ring compounds. The higher molecular weight open chain olefins may cyclize to aromatic ring compounds.

The feed stock in addition to the olefin and oxygen can contain one or more paraffins or naphthenic hydrocarbons having up to about ten carbon atoms, which may be present as impurities in some petroleum hydrocarbon stocks and which may also be dehydrogenated in some cases.

The amount of oxygen can be within the range of from about 0.3 to about 4 moles per mole of double-bond created. Stoichiometrically, 0.5 mole of oxygen is required for the dehydrogenation of one mole of monolefin to a diolefin. It is preferred to employ an excess of oxygen, e.g. an oxygen/olefin ratio of from 0.6 to about 3, in order to ensure a higher yield of diolefin per pass. The oxygen can be supplied as pure or substantially pure oxygen or as air.

When pure oxygen is used, it may be desirable to incorporate a diluent in the mixture such as steam, carbon dioxide or nitrogen.

The feed stock can be catalytically dehydrogenated in the presence of steam, but this is not essential. When steam is used, from about 0.1 to about 6 moles of steam per mole of olefin reactant is employed, but amounts larger than this can be used.

The dehydrogenation proceeds at temperatures within the range of from about 300° C. to about 1,000° C. Optimum yields are obtainable at temperatures within the range from about 400° C. to 550° C.

The preferred reaction pressure is approximately atmospheric, within the range of from about 0.1 to about 5 atmospheres.

Only a brief contact time with the catalyst is required for effective dehydrogenation. The apparent contact time with the catalyst can vary from about 0.1 up to about 50 seconds but higher contact times can be used if desired. At these contact times, comparatively small reactors and small amounts of catalyst can be used effectively.

Process Conditions

In carrying out the foregoing processes, any apparatus of the type suitable for carrying out oxidation reactions in the vapor phase may be employed. The processes may be conducted either continuously or intermittantly. The catalyst may be a fixed-bed employing a large particulate or pelleted catalyst or, in the alternative, a fluid-bed catalyst may be employed.

Catalyst

The catalysts employed in accordance with the present invention are oxide complexes of uranium and antimony promoted with various additional elements and can be described by the following general formula:

$$A_a B_b E_c U_d Sb_e O_x$$

wherein
  A is at least one element selected from Group IB and Group VB of the Periodic Table (Sargent-Welsh);
  B is at least one element selected from Group VIB;
  E is at least one element selected from Group IVA and Group IVB and thorium; and
wherein
  a is 0.001 to 10;
  b is 0.001 to 10;
  c is 0.001 to 10;
  d is 0.1 to 10;
  e is 1 to 20;
  x is determined by the valence requirements of the other elements present.

Preferably, A is at least one element selected from Cu, Ag, V, Nb and Ta; B is at least one element selected from W, Mo and Cr; and E is at least one element selected from Sn, Ge, Ti, Zr, Hf and Th. Also, a is preferably 0.01 to 5, more preferably 0.1 to 1.0; b is preferably 0.01 to 1, more preferably 0.01 to 0.05; c is preferably 0.1 to 5, more preferably 0.5 to 3; d is preferably 0.2 to 2, more preferably 0.5 to 1.5, most preferably 1; and e is preferably 1 to 10, more preferably 2 to 6, most preferably 3 to 6.

As will be noted, in such preferred catalysts the U/Sb ratio is preferably 1/10 to 1/1, more preferably 1/6 to ½, most preferably 1/6 to ⅓. Excellent catalysts are obtained when $0.1 < a+b+c < d+e$, and catalysts wherein $a+b+c+d < e$ are even more preferred. Most preferably, A is Cu and/or V; B is W and/or Mo; and E is Sn and/or Ti.

In addition to these elements, the catalyst can also contain minor amounts of promotors selected from the group Fe, Ni and Co. The amount of such promotors is between zero and 1 per U atom, more preferably between zero and 0.5.

These catalysts can be used either in unsupported form or supported on suitable carriers such as $SiO_2$, $Al_2O_3$, $BPO_4$, $SbPO_4$, $ZrO_2$, Alundum and the like. The catalysts can also be coated on these supports by special techniques known in the art.

These catalysts can be prepared by conventional techniques such as disclosed in the previously mentioned Callahan, et al. patent, U.S. Pat. No. 3,431,292.

EXAMPLES

In order to more thoroughly describe the present invention, the following working examples in which propylene was ammoxidized to acrylonitrile are presented. In these examples, the term "% yield" means

Comparative Examples A and B—$U_1Sb_{4.6}O_x+40\%$ $SiO_2$ 5 cc. of a catalyst of the above formula was charged into a fixed-bed micro-reactor and a feed comprising 1 propylene/1.1 $NH_3$/10.6 air/4 water was fed to the reactor at elevated temperature for a contact time of 6 seconds. The gross reaction product was recovered and analyzed. The results are set forth in the following Table I.

EXAMPLES 1 TO 6

In the same manner as described above in Comparative Example A, four different catalysts in accordance with the present invention were prepared. 5 cc. of each catalyst was charged into a fixed-bed micro-reactor and contacted with the same feed as described above in Comparative Examples A and B with a contact time of 6 seconds. The various reaction products produced were recovered and analyzed. The compositions of the different catalysts, the reaction temperatures and the results obtained are set forth in the following Table I.

TABLE I

| Example | Catalyst | React. Temp (°C.) | Yields AN | HCN |
|---|---|---|---|---|
| Comp. A | $U_1Sb_{4.6}O_x$ + 20% $SiO_2$ | 475 | 72.1 | 2.7 |
| Comp. B | " | 490 | 76.4 | 3.5 |
| 1 | $Cu_{0.4}W_{0.015}Sn_1U_1Sb_{4.6}O_x$ + 20% $SiO_2$ | 460 | 78.8 | 3.0 |
| 2 | $Cu_{0.4}W_{0.015}Sn_1U_1Sb_{4.6}O_x$ + 20% $SiO_2$ | 475 | 82.6 | 3.3 |
| 3 | $Cu_{0.8}W_{0.015}Sn_1U_1Sb_{4.6}O_x$ + 20% $SiO_2$ | 475 | 79.6 | 2.9 |
| 4 | $Cu_{0.4}W_{0.015}Sn_1Fe_{0.5}U_1Sb_{4.6}O_x$ + 20% $SiO_2$ | 475 | 76.6 | 2.9 |
| 5 | $Cu_{0.4}W_{0.015}Ti_1U_1Sb_{4.6}O_x$ + 20% $SiO_2$ | 475 | 81.9 | 1.9 |
| 6 | $Cu_{0.4}W_{0.015}Ti_1U_1Sb_{4.6}O_x$ + 20% $SiO_2$ | 490 | 78.9 | 3.9 |

From the foregoing, it can be seen that catalysts produced in accordance with the present invention provide significantly superior AN yields compared with the unpromoted base catalyst system.

Although only a few embodiments of the present invention have been described above, many modifications can be made without departing from the spirit and scope of the invention. All such modifications are intended to be included within the scope of the present invention, which is to be limited only by the following claims:

We claim:

1. A tin free uranium antimonate oxide complex catalyst of the formula:

$$A_aB_bE_cU_dSb_eO_x$$

wherein
A is at least one element selected from Group IB and Group VB of the Periodic Table;
B is at least one element selected from Group VIB;
E is at least one element selected from Group IVA and thorium; and wherein
a is 0.001 to 10;
b is 0.001 to 10;
c is 0.001 to 10;
d is 0.1 to 10;
e is 1 to 20;
x is determined by the valence requirements of the other elements present, the U/Sb ratio in said catalyst being 1/10 to 1/1.

2. The catalyst of claim 1 wherein a is 0.01 to 5, b is 0.01 to 1, c is 0.1 to 5, d is 0.2 to 2, and e is 1 to 10.

3. The catalyst of claim 2 wherein a is 0.1 to 1.0, b is 0.01 to 0.05, c is 0.5 to 3, d is 0.5 to 1.5, and e is 2 to 6.

4. The catalyst of claim 3 wherein e is 3 to 6.

5. The catalyst of claim 4 wherein $0.1 < a+b+c < d+e$.

6. The catalyst of claim 2 wherein $0.1 < a+b+c < d+e$.

7. The catalyst of claim 6 wherein $a+b+c+d < e$.

8. The catalyst of claim 2 wherein A is at least one element selected from Cu, Ag, V, Nb and Ta, wherein B is at least one element selected from W, Mo and Cr, and wherein E is at least one element selected from Ge, Ti, Zr, Hf and Th.

9. The catalyst of claim 8 wherein A is Cu and/or V, wherein B is W and/or Mo and E is Sn and/or Ti.

10. The catalyst of claim 8 wherein promoter elements selected from Fe, Ni and/or Co are incorporated at a level of between zero and 1 per gram atom of U.

11. The catalyst of claim 1 wherein the U/Sb ratio is 1/6 to $\frac{1}{2}$.

12. The catalyst of claim 11 wherein $0.1 < a+b+c < d+e$ and further wherein $a+b+c+d < e$.

13. The catalyst of claim 1 wherein the U/Sb ratio is 1/6 to $\frac{1}{3}$.

14. The catalyst of claim 13 wherein $0.1 < a+b+c < d+e$ and further wherein $a+b+c+d < e$.

15. The catalyst of claim 14 wherein A is at least one element selected from Cu, Ag, V, Nb and Ta, wherein B is at least one element selected from W, Mo and Cr, and wherein E is at least one element selected from Sn, Ge, Ti, Zr, Hf and Th.

* * * * *